US009259322B2

(12) United States Patent
Embleton et al.

(10) Patent No.: US 9,259,322 B2
(45) Date of Patent: Feb. 16, 2016

(54) CANINE INTERNAL STIFLE STABILIZATION (CISS) SYSTEM

(71) Applicant: Embark Enterprises Inc., Sundre (CA)

(72) Inventors: Neil Embleton, Sundre (CA); Veronica Barkowski, Sundre (CA)

(73) Assignee: Embark Enterprises, Inc., Sundre, AB (CA)

(*) Notice: Subject to any disclaimer, the term of this patent is extended or adjusted under 35 U.S.C. 154(b) by 0 days.

(21) Appl. No.: 14/203,342

(22) Filed: Mar. 10, 2014

(65) Prior Publication Data

US 2014/0277531 A1   Sep. 18, 2014

Related U.S. Application Data

(60) Provisional application No. 61/776,735, filed on Mar. 11, 2013, provisional application No. 61/778,324, filed on Mar. 12, 2013.

(51) Int. Cl.
*A61F 2/38* (2006.01)
*A61B 17/80* (2006.01)
*A61B 17/56* (2006.01)

(52) U.S. Cl.
CPC ............ *A61F 2/3854* (2013.01); *A61B 17/56* (2013.01); *A61B 17/8023* (2013.01); *A61B 17/8061* (2013.01); *A61B 2017/567* (2013.01)

(58) Field of Classification Search
CPC ................. A61F 2/38–2/389; A61F 2002/38; A61F 2250/0081; A61B 17/8061; A61B 17/8023; A61B 2017/567
USPC .......... 623/18.11, 20.14, 19.12, 20.22, 21.13, 623/21.16
See application file for complete search history.

(56) References Cited

U.S. PATENT DOCUMENTS 4,224,697 A * 9/1980 Murray et al. ............. 623/20.25
5,443,444 A 8/1995 Pruyssers
(Continued)

OTHER PUBLICATIONS

International Search Report of the International Searching Authority mailed Oct. 23, 2014 issued in connection with International Patent Application No. PCT/IB2014/001242 (4 pages).
(Continued)

*Primary Examiner* — Alvin Stewart
(74) *Attorney, Agent, or Firm* — McCarter & English, LLP

(57) ABSTRACT

A Canine internal stifle stabilizing (CISS) system is provided as a three part modular, stifle stabilizing device that can be permanently or temporarily surgically implanted and attached onto the medial side of the distal femur and proximal tibia of quadrupeds. The stabilizing device is centered over the medial aspect of the quadruped stifle joint. The device includes three parts: a femoral component, a tibial component and an articular sliding insert component. The tibial and femoral components are fastened to the medial aspect of the femur and tibia by a varying number of fasteners. The distal end of the femoral component contains a ball and stem. The ball and stem is attached to the femoral component. The proximal tibial component has a rectangular space that accepts and holds the articular sliding insert component, such as by a pressure fit into the rectangular space provided on the proximal tibial component. The articular sliding insert component includes a groove that accepts and holds the ball that is attached to the femoral component. This locks the femoral and tibial components together. Also on the underside of the articular sliding insert component is a flange. In operation, the flange is located between the femoral and tibial components and has a bevelled edge (for example a ten (10) degree bevelled edge) on either side. This bevelled edge allows for a maximum internal and external rotation of the stabilized stifle joint. This device permits normal stifle joint movement in all planes, while continually providing support.

22 Claims, 13 Drawing Sheets

(56) References Cited

U.S. PATENT DOCUMENTS

| | | | |
|---|---|---|---|
| 6,033,373 | A | 3/2000 | Davis et al. |
| D463,557 | S | 9/2002 | Bryant et al. |
| D480,141 | S | 9/2003 | Benirschke et al. |
| D481,460 | S | 10/2003 | Doty et al. |
| 6,656,144 | B1 | 12/2003 | Coligado |
| 6,764,244 | B2 | 7/2004 | Pansiera |
| 7,029,475 | B2 * | 4/2006 | Panjabi .................. 606/279 |
| D586,918 | S | 2/2009 | Simons |
| 7,611,540 | B2 * | 11/2009 | Clifford et al. ............ 623/20.21 |
| D606,195 | S | 12/2009 | Eisen et al. |
| 7,655,041 | B2 * | 2/2010 | Clifford et al. ............ 623/13.12 |
| D622,853 | S | 8/2010 | Raven, III |
| D648,027 | S | 11/2011 | Vancelette et al. |
| D652,926 | S | 1/2012 | Braido |
| 8,088,166 | B2 * | 1/2012 | Makower et al. .......... 623/20.14 |
| 8,142,510 | B2 | 3/2012 | Lee et al. |
| 8,152,035 | B2 | 4/2012 | Earl |
| 8,470,048 | B2 * | 6/2013 | Wolfson et al. ............ 623/20.33 |
| 8,523,948 | B2 * | 9/2013 | Slone et al. ................ 623/18.11 |
| 8,545,571 | B2 * | 10/2013 | Collazo et al. ............ 623/20.27 |
| D699,351 | S | 2/2014 | Podgorski et al. |
| 8,709,090 | B2 * | 4/2014 | Makower et al. .......... 623/20.21 |
| 8,715,359 | B2 * | 5/2014 | Deffenbaugh et al. .... 623/20.29 |
| 8,801,795 | B2 * | 8/2014 | Makower et al. .......... 623/20.21 |
| D717,433 | S | 11/2014 | Samani et al. |
| 8,894,714 | B2 * | 11/2014 | Makower et al. .......... 623/20.21 |
| 9,005,298 | B2 * | 4/2015 | Makower et al. .......... 623/20.14 |
| 2002/0151978 | A1 * | 10/2002 | Zacouto et al. ............ 623/17.12 |
| 2003/0153856 | A1 | 8/2003 | Seligman et al. |
| 2004/0220675 | A1 | 11/2004 | Lewis et al. |
| 2005/0049708 | A1 * | 3/2005 | Atkinson et al. ........... 623/17.16 |
| 2005/0055100 | A1 | 3/2005 | Lewis et al. |
| 2006/0064169 | A1 * | 3/2006 | Ferree ....................... 623/17.12 |
| 2007/0276305 | A1 | 11/2007 | Kahlmeyer et al. |
| 2008/0275561 | A1 * | 11/2008 | Clifford et al. ............ 623/20.21 |
| 2008/0275562 | A1 * | 11/2008 | Clifford et al. ............ 623/20.21 |
| 2009/0299244 | A1 | 12/2009 | Chiang et al. |
| 2011/0054370 | A1 | 3/2011 | Perry |
| 2012/0053587 | A1 | 3/2012 | Kiritsis |
| 2012/0123551 | A1 * | 5/2012 | Landry et al. ............. 623/20.21 |
| 2012/0253347 | A1 | 10/2012 | Murashko, Jr. |
| 2013/0041375 | A1 | 2/2013 | Fierlbeck et al. |
| 2014/0214036 | A1 | 7/2014 | Weiner et al. |
| 2014/0236154 | A1 | 8/2014 | Liao et al. |
| 2014/0257292 | A1 | 9/2014 | Embleton et al. |

OTHER PUBLICATIONS

Written Opinion of the International Searching Authority mailed Oct. 23, 2014, issued in connection with International Patent Appln. No. PCT/IB2014/001242 (3 pages).

Examiner's Report dated Jan. 27, 2015 issued in connection with Canadian Patent Application No. 158599 (2 pages).

Notice of Allowance dated Apr. 1, 2015, from pending U.S. Appl. No. 29/484,500 (11 pages).

* cited by examiner

Section A-A

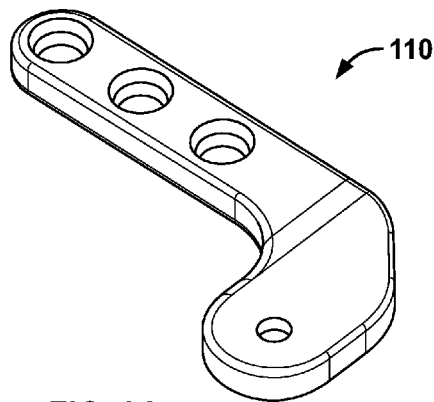
FIG. 8A
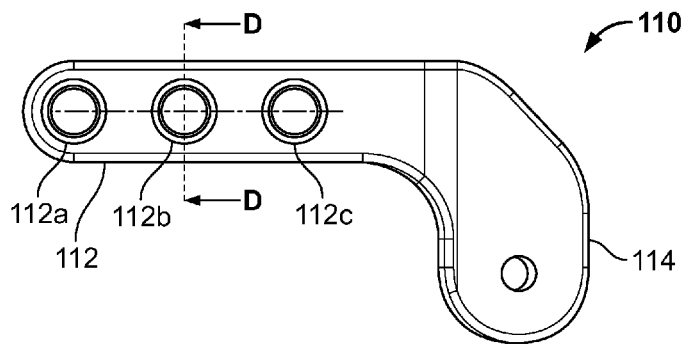
FIG. 8B
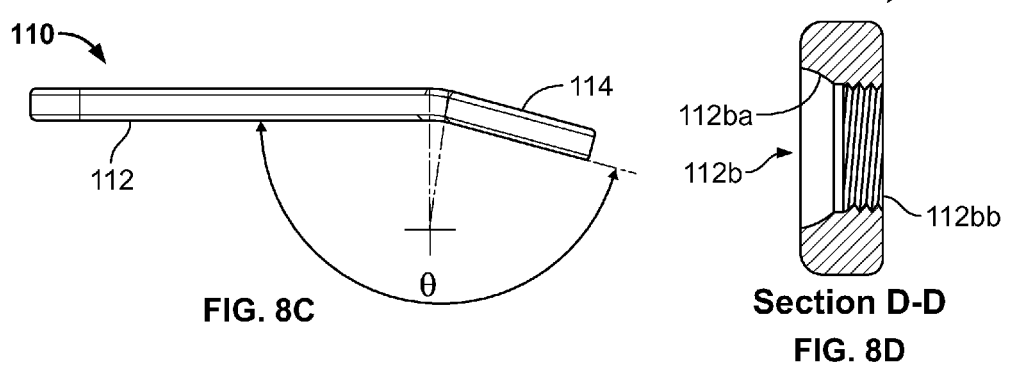
FIG. 8C
Section D-D
FIG. 8D

CANINE INTERNAL STIFLE STABILIZATION (CISS) SYSTEM

CROSS-REFERENCE TO RELATED APPLICATIONS

This application claims the benefit of U.S. Provisional Patent Application No. 61/776,735, filed on Mar. 11, 2013 and U.S. Provisional Patent Application No. 61/778,324, filed on Mar. 12, 2013, the entire disclosures of which are expressly incorporated herein by reference.

BACKGROUND OF THE INVENTION

1. Technical Field

The present invention relates to a method and apparatus veterinary orthopedic surgical stabilization of an unstable quadruped stifle joint.

2. Related Art

The quadruped stifle is a complex and powerful joint that is stabilized by four main ligaments: the cranial cruciate, the caudal cruciate, the medial collateral and the lateral collateral. The stifle joint is further stabilized by the patella and the tendons associated therewith and the surrounding musculature. These powerful ligaments and tendons bind the femur and tibia together. Although the structure of the stifle provides one of the strongest joints of the quadruped body, as in humans, the stifle joint is also one of the most frequently injured joints. The most frequent injury occurs to the cranial cruciate ligament. The canine is the most frequently affected quadruped species. The large number of canine cranial cruciate ligament injuries has given rise to a considerable number of innovative surgical procedures and devices for attempting to replace the partially or completely torn or avulsed cranial cruciate ligament. A partially, or completely torn, stifle associated ligament or tendon typically results in serious clinical symptoms such as stifle swelling and inflammation, significant stifle pain, disuse muscular atrophy, radiographic evidence of arthritis and stifle joint instability, resulting in a significantly diminished ability to perform high level, or daily activities relating to mobility. The inevitable long term effects of a damaged and unstable quadruped stifle joint include significant meniscal and articular cartilage damage to the femur, tibia and patella. This leads to chronic pain and debilitating degenerative joint disease.

Injuries to any of the ligaments or tendons (including the cranial cruciate ligament) of the quadruped stifle typically require a major surgical intervention to repair the damage. Historically and currently these attempts at repair have involved both intra-articular and extra-articular repair procedures with varying degrees of success. More recently geometric modification of the canine stifle joint has been advocated.

As a result, several types of surgical procedures have been developed and are currently in use to attempt to mitigate the instability of the canine stifle caused by the damaged cranial cruciate ligament and/or other ligaments and tendons. Although primary cranial cruciate ligament repair would be ideal, it is unfortunately not a viable option in veterinary medicine. There are several reasons why primary repair is not viable: cranial cruciate injury in quadrupeds is rarely acute, it progresses over time and the amount of trauma that occurs to the cranial cruciate ligament is usually very severe. As a result the torn ends of the cranial cruciate ligament are not of a sufficient length to reattach successfully or have been resorbed to an extent that reattachment is not possible.

Historically intra-articular stabilization of the cranial cruciate deficient canine stifle was performed via placement of an autogenous graft, harvested either from the patella tendon or the tensor fascia lata. This method involved harvesting of the graft and then tunnelling the graft through the stifle joint and attaching so that it mimics the cranial cruciate ligament. This method has fallen out of favor due to the invasiveness of the surgical procedure required, the inherent weakness of the graft and high rate of failure of the autogenous grafting material.

All other current techniques involve extracapsular, or outside the joint repair methods. Numerous terms and techniques are utilized. One extra-capsular repair technique utilizes a synthetic nylon (commercial fishing line) or a braided polymer material. These methods both generally ultimately fail. The nylon material cycles, weakens and breaks due to movement of the stifle joint. The braided polymer material, while much stronger, either breaks, cuts through the bone, or as a result of being braided, becomes infected. These current techniques have been successful in reducing abnormal femoral/tibial movement in a sagittal plane. However, neither of these current extracapsular repair techniques permits the tibia, in relation to the femur, to internally and externally rotate as in a normal joint, nor do they permit normal compression and extension.

Another class of cranial cruciate repair surgery is the geometric modification of the quadruped stifle joint. There are currently two accepted geometric modification procedures: The tibial plateau leveling surgical osteotomy (TPLO) of the proximal tibia and tibial tuberosity advancement (TTA). The TPLO procedure involves a full thickness semi-circular osteotomy below the proximal tibia. The proximal portion of the tibial bone is then rotated counter-clockwise to decrease the tibial slope and therefore, associated cranial tibial thrust. The rotated bone is fixed in place using a specialized bone plate. The TTA procedure involves an angled, vertical cut of the tibial tuberosity. The freed portion is then advanced and fixed into place using specialized bone plating equipment. Both procedures require a very invasive surgical procedure that accomplishes its goal of decreasing cranial tibial thrust by either, transposing or rotating the cut proximal piece of tibia. The current issues surrounding these repair methods center around the requirement that, either, the caudal cruciate (TPLO) or the central patellar tendon (TTA) is required to act as the cranial cruciate ligament—a task, neither tissue was designed to do. Other issues with geometric repair methods include: the limited access of veterinarians capable of performing the procedures due to the specialized training and expensive equipment required for both the TPLO and TTA procedures. Perhaps the most alarming concern, with either of these procedures, is there is no attempt made to limit the internal rotation of the tibia relative to the femur. This is one of the primary jobs of the quadruped, cranial cruciate ligament. This is particularly important when considering that during certain parts of the stride, the quadruped stifle joint is non-weight bearing and unsupported. It is during this non-weight bearing period that internal rotation of the tibia is unrestricted greatly increasing the risk that additional quadruped stifle joint trauma can, will, and does, occur at this time.

Other ligament or tendon injuries to the quadruped stifle require different procedures to repair the damage. Many of these procedures have varying success rates.

To date no one procedure exists to stabilize an unstable, injured, or fractured quadruped stifle. Accordingly, what is needed in this art is a method of providing continuous support to the damaged, quadruped stifle during both non weight bearing and full weight bearing periods. This surgical procedure uses a surgically implanted modular quadruped stifle stabilizing device that offers continuous support, while allowing the quadruped stifle to flex, extend, internally and externally rotate, and expand and compress normally during all phases of the stride.

SUMMARY

A surgical procedure and apparatus is provided for biocompatible, modular surgical stifle stabilization that can be permanently, or temporarily, implanted on the medial side of the distal femur and proximal tibia to stabilize an unstable, quadruped, stifle joint.

The apparatus provides continuous support to the injured quadruped stifle, while permitting the quadruped stifle to move in a normal manner during all phases of the quadruped stride. The apparatus permits normal flexion and extension and also allows for a normal internal and external rotation. Stifle joint compression and expansion is also permitted.

This procedure and apparatus is indicated in cranial cruciate rupture, caudal cruciate rupture, medial collateral rupture, lateral collateral rupture, medial patellar luxation, lateral patellar luxation, patellar tendon avulsion, patellar fracture, proximal tibial fracture, distal femoral fracture, stifle disruption and any combination, or degree of any of the above conditions.

BRIEF DESCRIPTION OF THE DRAWINGS

The foregoing features of the disclosure will be apparent from the following Detailed Description of the Disclosure, taken in connection with the accompanying drawings, in which:

FIGS. 8A-8C are perspective front, and side views of the tibial component shown in FIG. 6, and FIG. 8D is a cross-sectional view taken along line D-D in FIG. 8C;

DETAILED DESCRIPTION

A modular surgically implanted apparatus is disclosed that can be used in canine, feline and other quadruped animal species, both domestic and exotic, to stabilize an unstable stifle joint that may be due to any number of causes, for example, soft tissue or hard tissue injury of the stifle ligaments, tendons and their attachments and surrounding structures. The system works for primary treatment for a partial or complete cranial cruciate ligament injury or avulsion, a partial or complete caudal cruciate ligament injury or avulsion, a partial or complete medial collateral ligament injury or avulsion, a partial or complete lateral collateral ligament injury or avulsion, a congenital or traumatic medial patellar luxation or avulsion, a congenital or traumatic lateral patellar luxation or avulsion, a patellar fracture, or any combination of, or all of the above.

The Canine Internal Stifle Stabilizing (CISS) system provides continuous support and allows for the normal extension (e.g., 160 degrees) and flexion (e.g., 40 degrees) range of motion of the stifle joint, tibia in relation to the femur, during weight bearing and non-weight bearing periods. In the canine patient, the angle of the stifle is measured from the lateral side. It is the angle formed by an intersecting line bisecting the center of the femur and tibia. In the normal canine patient, the stifle range of motion is approximately from one hundred and sixty (160) degrees in full extension to forty (40) degrees in full flexion. The CISS system provides for normal internal (e.g., 25 degrees as measure at the foot) and external (e.g., 15 degrees as measured at the foot) tibial rotation. Tibial rotation is measured as the amount of inward or outward twisting of the tibia relative to the femur. In the normal canine patient the normal maximum internal tibial rotation, relative to the femur, is generally about twenty-five (25) degrees measured at the foot. The normal maximum external rotation, relative to the femur, is generally about fifteen (15) degrees measured at the foot. The proximal tibia rotates about 10 degrees in either external or internal rotation.

Figure 1:
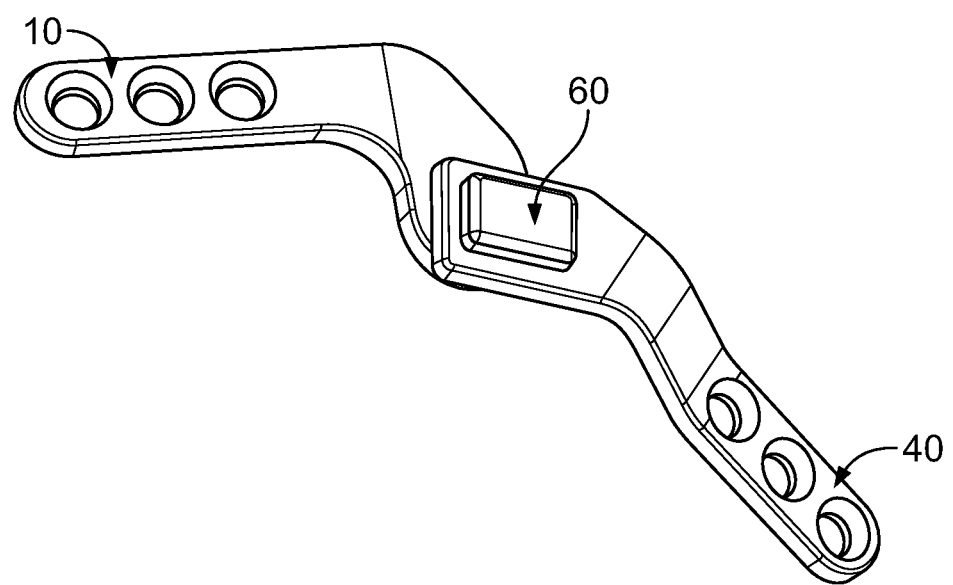
FIG. 1 is a perspective view of the apparatus fully assembled, including the femoral component, the tibial component and the articular sliding insert component.

Referring to FIG. 1, the CISS system is shown as a surgically implanted, modular stifle stabilizing device comprising three components: the femoral component 10, the tibial component 40, and the articular sliding insert component 60. Each stabilizing component can be a separately manufactured component that is interconnected to the next component. These connections between the components allow the individual components to maintain the normal range of motion and normal external and internal rotation of the canine, feline or other quadruped stifle, while continuously stabilizing the stifle joint.

Figure 2A:
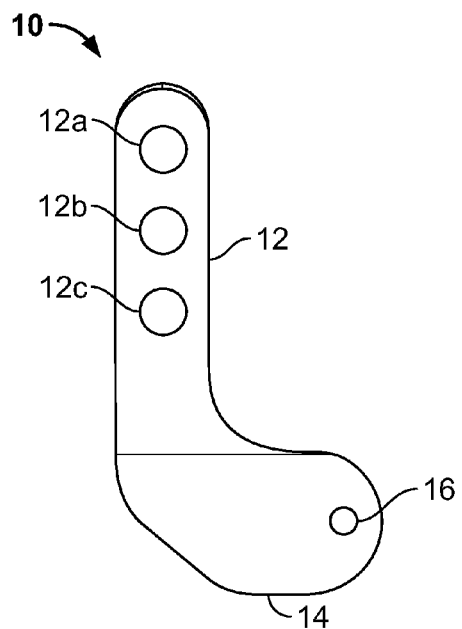
FIGS. 2A-2D are front, side, perspective and end view, respectively, of the femoral component.
Figure 2B:
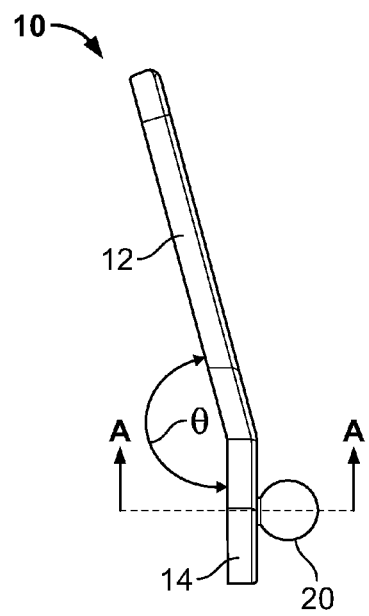

Referring to FIGS. 2A-2D, the femoral component 10 is a form fitting, generally "L" shaped, curved component that conforms and can be permanently, or temporarily attached to the contour of the medial third of the distal femur. The femoral component 10 includes a leg portion 12 and a bottom portion 14, which can be positioned at an angle Θ with respect to leg portion 12 as shown in FIG. 2B. The leg portion 12 can have front and back generally planar faces and opposing, generally planar edges. At the distal end, the edges can terminate in a rounded distal edge. The bottom portion 14 includes front and back generally planar faces and an edge that defines a bulbous shape. The femoral component 10 can be made from a number of acceptable, biocompatible, implantable materials. These materials include, but are not limited to, 316MVL stainless steel, titanium or UHMWPE.

Exposed edges of the femoral component 10 can be rounded and smooth. The length of the femoral component 10 can vary with the size of patient. However, the size range is approximately 30-60 mm in length, and approximately 10-35 mm in width. Similarly, the thickness of the femoral component 10 can vary with the size of the patient. However, generally the thickness is in the range of about 2-3 mm. The dimensions of the femoral component 10 can vary with the different sizes that are produced and can be based wholly or in part on the body weight of the patient.

The femoral component 10 contains attachment holes in leg 12 such as two (2) to three (3) permanent attachment holes, 12a, 12b and 12c. These holes can be aligned and extend through the front and back generally planar faces. The diameter of these holes can vary such that they will accept the appropriate sized screw, or other fastener. For example, the holes 12a, 12b and 12c could be 3.5 mm in diameter, to allow for the placement of a 3.5 mm cortical bone screw. The holes 12a, 12b and 12c can be sized to have a sufficient diameter such that the head of the screw, such as a 3.5 mm cortical screw, fits flush with the femoral component 10. Other sized bone screws, such as 2.0 mm, 2.7 mm, or 3.5 mm cortical bone screws can also be used, and the holes 12a, 12b and 12c could be sized accordingly. The distal end of the femoral component 10 can be contoured to be elevated away from the bone of the distal femur so as not to impede femoral soft tissues. Accordingly, a clearance of 1-2 mm can be provided.

Figure 2C:
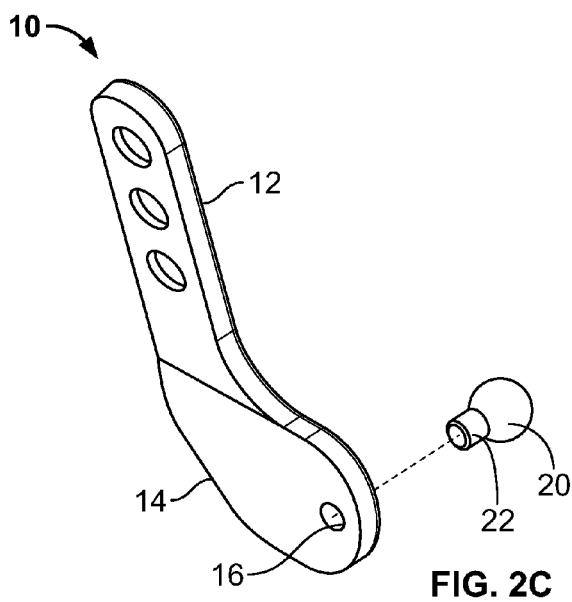
Figure 2D:
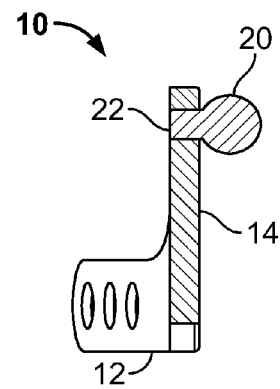

As shown in FIGS. 2C and 2D, a ball 20 and stem 22 are located on the bottom portion 14 of the femoral component 10. The stem 22 is received by aperture 16, and the ball extends outward from the outer surface of the femoral component 10 at 90 degrees. The ball 20 and stem 22 can be formed separately and joined together or they can be of a unitary construction. The stem 22 can be pressure fit into an aperture 16 in the bottom portion 14. Other methods of attachment, however, can be employed. For example, aperture 16 and stem 22 could be threadably engaged. Similarly, stem 22 could be threadably engaged with ball 20. The shape of ball 20 can be varied as desired provided it can interlocked with the tibial component 40, such as by way of insert component 60, as will be described. This forms the articulation point on the femoral component 10. The ball 20 engages the articular sliding insert component which is in turn inserted into the tibial component, as will be described. The ball 20 permits the stifle joint complete and continuous support during both full extension and full flexion from approximately one hundred and sixty (160) degrees (full extension) to approximately forty (40) degrees (full flexion).

Figure 3A:
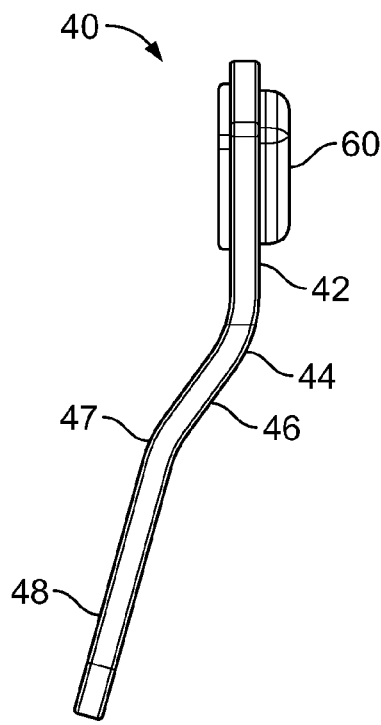
FIGS. 3A-3C are side, front and perspective views, respectively, of the tibial component and the articular sliding insert component (FIG. 3C)
Figure 3B:
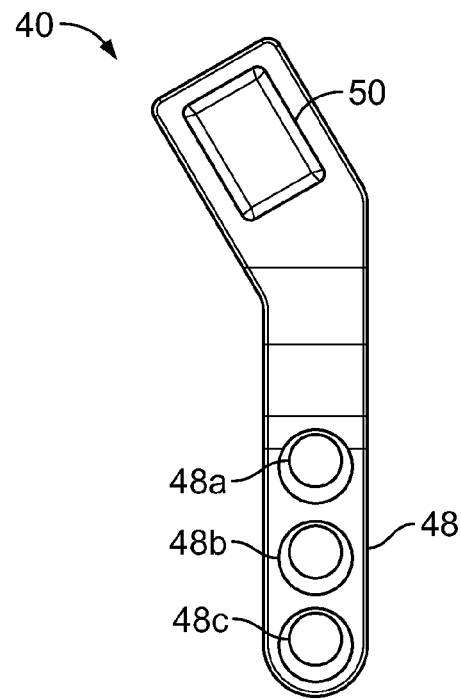
Figure 3C:
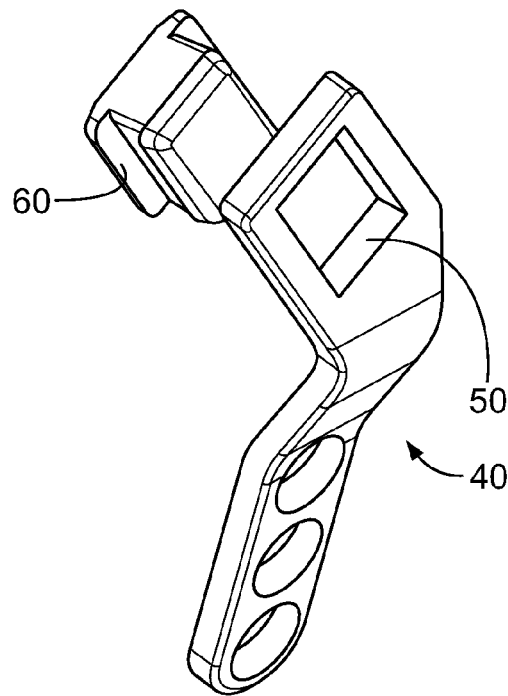

Referring to FIGS. 3A-3C, the tibial component 40 conforms to the contours of the proximal medial tibia. The tibial component 40 is a curved having a first proximal planar portion 42, a first bend 44, a second central planar portion 46, a second bend 47 and a third distal planar portion 48. The tibial component 40 can be made from a number of acceptable, biocompatible, implantable materials. These materials include, but are not limited to, 316MVL stainless steel, titanium or UHMWPE. Exposed edges of the tibial component 40 can be rounded and smooth. The length of the tibial component 40 can vary with the size of patient. However, the size range is approximately 30-60 mm in length, and approximately 10-35 mm in width. The thickness of the tibial component 40 can also vary with the size of the patient. However, generally the thickness is in the range of about 2-3 mm. The second central planar portion 44 and the distal planar portion 48 include front and back general planar faces and opposing generally planar edges. At the distal edge, the edges terminate in a rounded distal edge. The tibial component 40 contains attachment holes in third distal planar portion 48, such as two to three permanent holes 48a, 48b and 48c, for attachment to the tibia. The diameter of these holes can be sized such that they will accept the appropriate sized screw, or other fastener. For example, the holes 48a, 48b and 48c could be 3.5 mm in diameter, to allow for the placement of a 3.5 mm cortical bone screw. The holes 48a, 48b and 48c can be sized to have a sufficient diameter such that the head of the screw, such as a 3.5 mm cortical screw, will fit flush with the tibial component 40. Other sizes, such as 2.0 mm, 2.7 mm, or 3.5 mm cortical bone screws can also be used, and the holes 48a, 48b and 48c can be sized accordingly. The attachment holes can be sized such that they will accept the appropriate sized screw and so that the screw is flush when implanted. The proximal part of the tibial component 40 can rise about 1-2 mm off the medial surface of the proximal tibia to allow for the clearance of the soft tissues of the proximal stifle. The first proximal planar portion 42 of the tibial component 40 has wider edge to edge front and back generally planar faces and includes a slot, such as a rectangular slot 50, extending through the front and back generally planar faces. This rectangular slot 50 on the tibial component 40 receives, such as by a pressure fit attachment, the articular sliding insert component 60. The rectangular slot 50 allows the articular sliding insert component to be firmly held in place. Other ways of connecting the insert component 60 to the tibia component 40 and the femoral component 10 to the insert component 60 are considered to be with the scope of this disclosure.

Figure 4A:
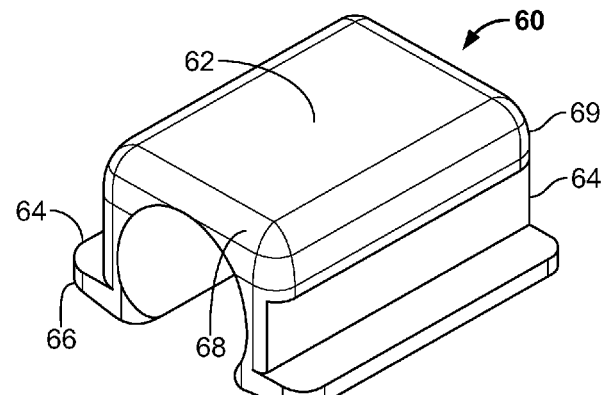
FIGS. 4A-4E are detailed perspective, top, cross-sectional, side and bottom views, respectively, of the articular sliding insert component.
Figure 4B:
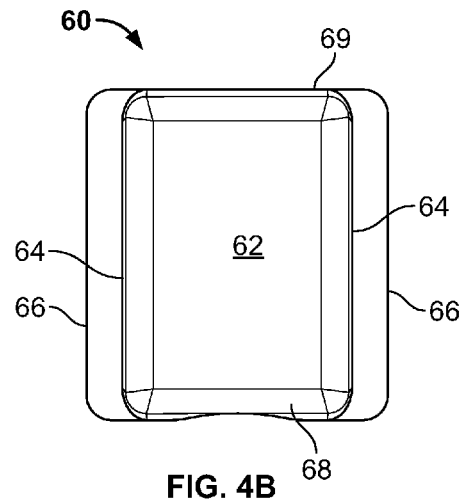
Figure 4C:
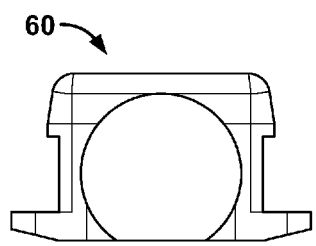
Figure 4D:
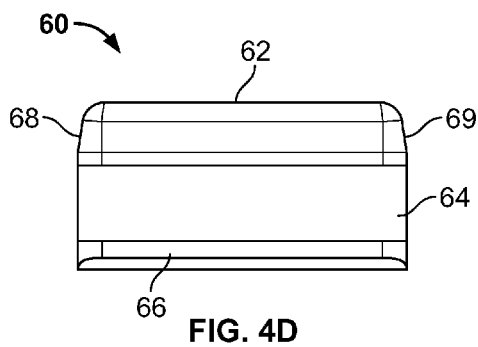
Figure 4E:
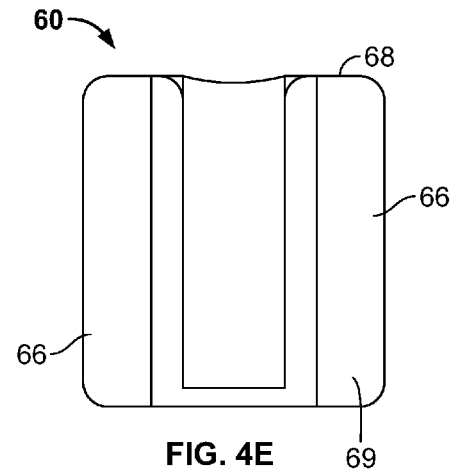

Referring to FIGS. 4A-4E, the articular sliding insert component 60, or intermediate component comprises a rectangular-shaped component that conforms to the rectangular opening 50 of the tibial component 40. The articular sliding insert component 60 can be made of a biocompatible, surgically implantable material that preferably has good wear characteristics, is inert and carries a low coefficient of friction. As such, the insert component could be made of a plastic such as a Ultra High Molecular Weight Polyethelene (UHMWPE) material. The articular sliding insert component 60 fits into and is received by an appropriately sized rectangular slot 50 of the proximal tibial component 40. The insert 60 could be secured in the tibial component 40 by a pressure fit or otherwise. The articular sliding insert component 60 has a top 62 and side walls 64 surrounding a central channel, and includes angled flange extensions 66 extending outwardly from the lower ends of sidewalls 64. The flanges 66 extend to and contact the tibial component 40 when inserted into slot 50. As shown in FIG. 4C, the central channel is cylindrical shaped, and can be open at one or both of the forward and rear sides 68 and 69 along the lower side. The articular central cavity of sliding insert component 60 is configured to accept and interlock with the circular ball 20 attached to the femoral component 10. This allows the femoral ball 20 to be captured and held in place during all phases of the stride. One end of the insert could have a wall that closes one end of the cavity. The tibial component, where attached to the insert, closes off one or both ends of the cavity to prevent the ball from escaping the cavity. The flanges 66 provide continual separation of both the tibial and femoral components. This extension can be angled to allow approximately ten (10) degrees of internal and external rotation of the tibial component 40. The rotation is limited to approximately ten (10) degrees of internal rotation and ten (10) degrees of external rotation by the angled flanges 66. The relationship between the tibial component 40 and the articular sliding insert component 60 allows for the independent internal and external rotation of the tibia while continuously providing support for the stifle throughout the normal flexion and extension of the quadruped stifle joint.

The articular sliding insert component 60 allows for the internal and external rotation at any phase of extension or flexion.

The cylindrical shaped central channel is sized and shaped to correspond with the size and shape of the ball attached to the femoral component. As such, the connection between the cylindrical channel and the ball creates a ball and socket type joint that allows for rotational and pivotal or swivel movement of the ball with respect to the channel, and accordingly, allows for such movement of the femur with respect to the intermediate component and the tibial component. Further, the channel allows for the ball to slide from end to end along the length of the channel thereby providing for additional translational movement of the ball with respect to the channel, and accordingly, allows for such movement of the femoral component with respect to the intermediate component and the tibial component. When assembled, the insert component can be maintained in position with respect to the tibial component by virtue of the tibial component fitting between the lower flanges of the intermediate component and corresponding shoulders positioned in facing relationship thereto. Although the intermediate component and the space therefore in the tibial component has been shown and described as having a rectangular shape, the shape could take on any suitable form.

Figure 5A:
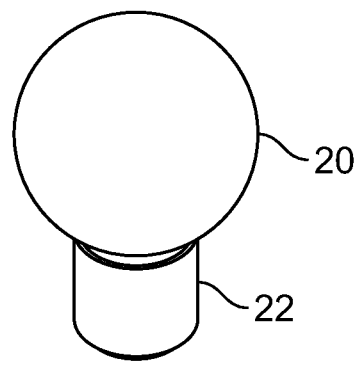
FIGS. 5A-5C are perspective, side and bottom views, respectively, of the detailed femoral ball and stem of the apparatus.
Figure 5B:
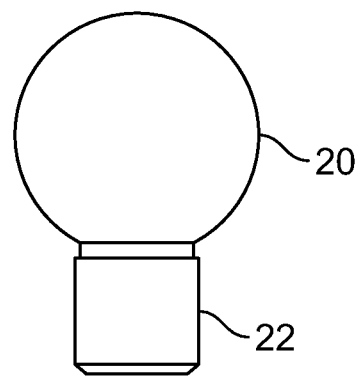
Figure 5C:
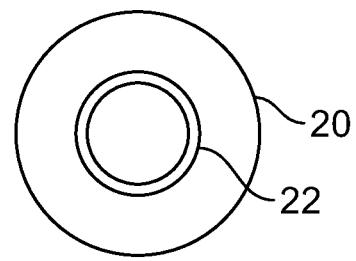

FIGS. 5A-5C show views of the ball 20 and stem 22 that connects with the femoral component 10 and the articular sliding component 60. Like the femoral and tibial components, the ball and stem can be made of a biocompatible material.

Figure 7:
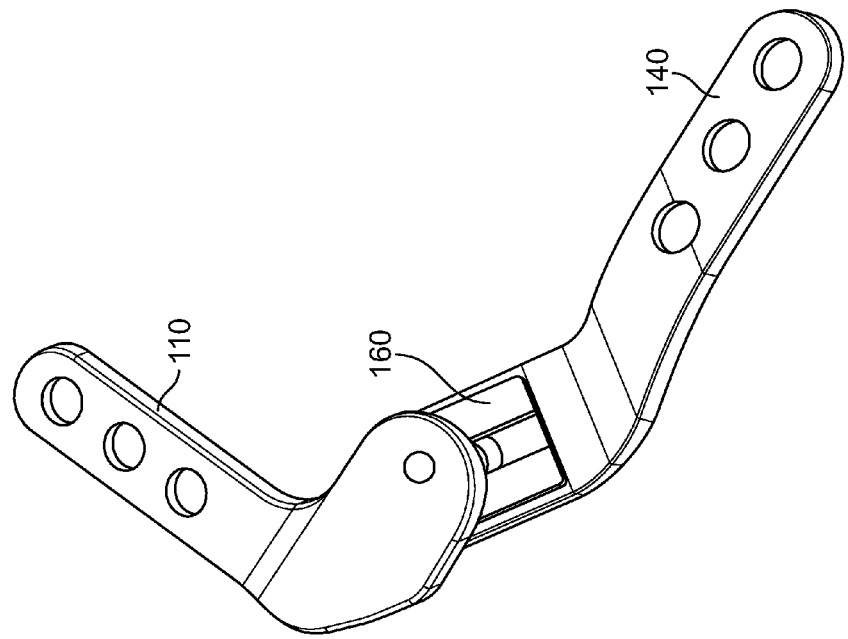
FIG. 7 is a bottom view of the apparatus shown in FIG. 6.
Figure 6:
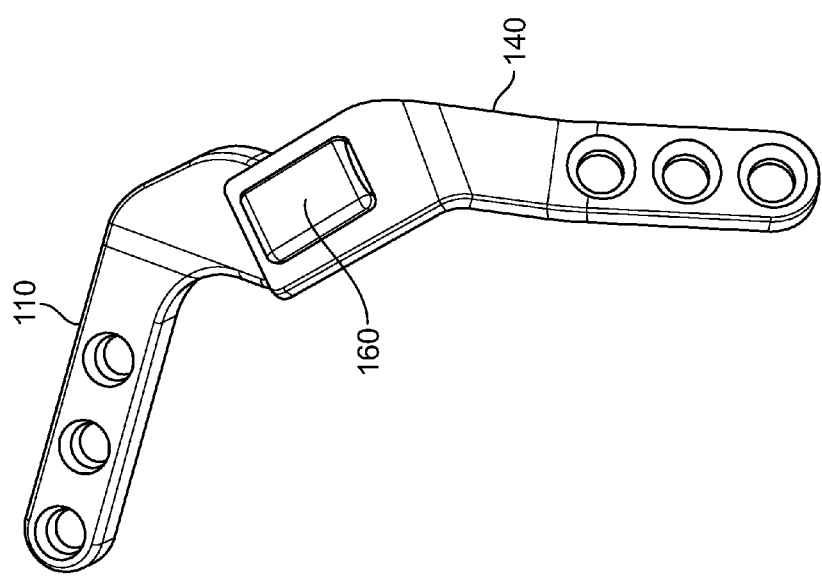
FIG. 6 is another front view of an apparatus fully assembled.

FIG. 6 is another view of a fully assembled apparatus showing the femoral component 110, the tibial component 140 and the insert component 160. FIG. 7 is a bottom view thereof.

Figure 9:
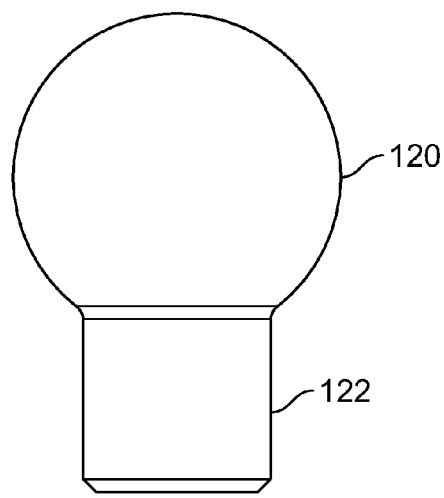
FIG. 9 is a side view of a ball and stem.

FIG. 8A is another perspective view of the femoral component 110. FIG. 8B is a front view of the femoral component showing the leg portion 112 and bottom portion 114. FIG. 8C is a side view of the femoral component showing angle Θ, leg portion 112 and bottom portion 114. FIG. 8D is a cross-sectional view taken along line D-D on FIG. 8B showing an aperture 112B that could be partially threaded at one area 112BB while having a unthreaded recessed area 112BA. Any suitably configured aperture could be used in the femoral or tibial component. FIG. 9 shows a side view of the ball 120 and stem 122.

Figure 10:
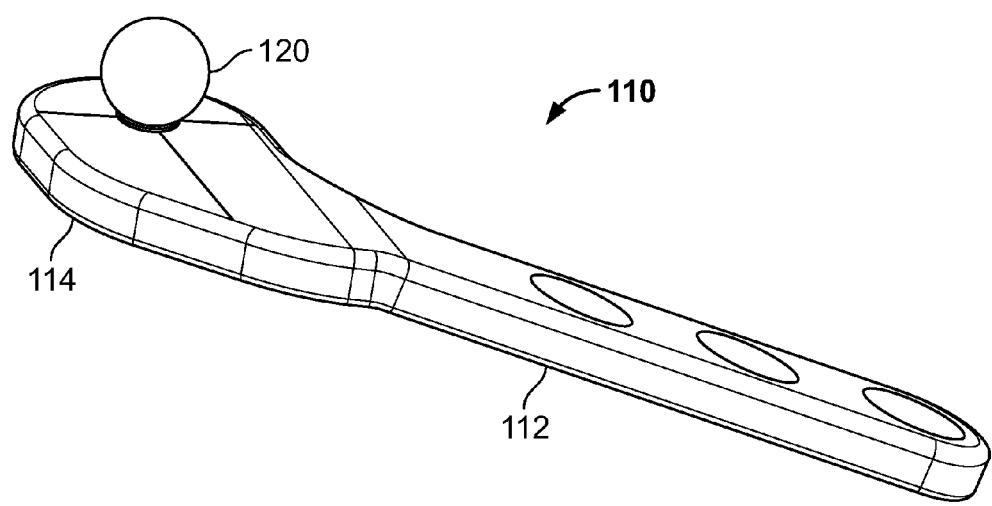
FIG. 10 is a perspective view of the ball and stem shown in FIG. 9 attached to the femoral component.

As shown in FIG. 10 the ball 120 is attached to the femoral component 110 at the bottom portion 114 by inserting the stem of the ball into the aperture in the femoral component.

Figure 11A:
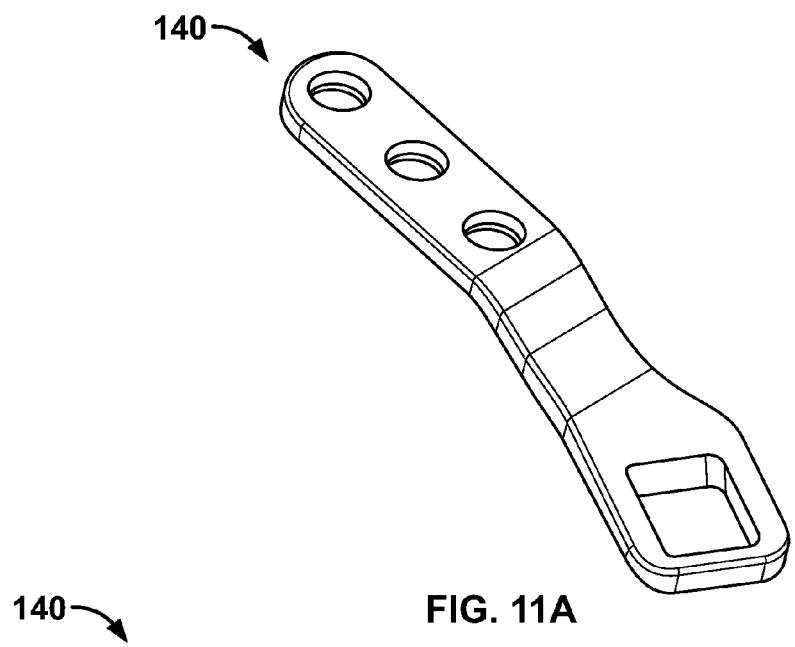
FIGS. 11A-11C are perspective, front and side views of the tibial component.
Figure 11B:
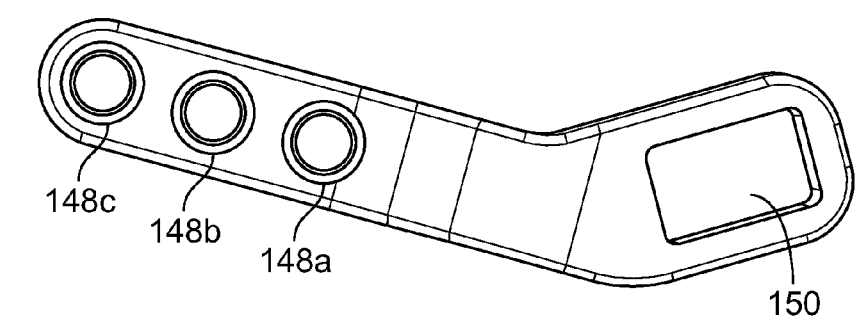
Figure 11C:
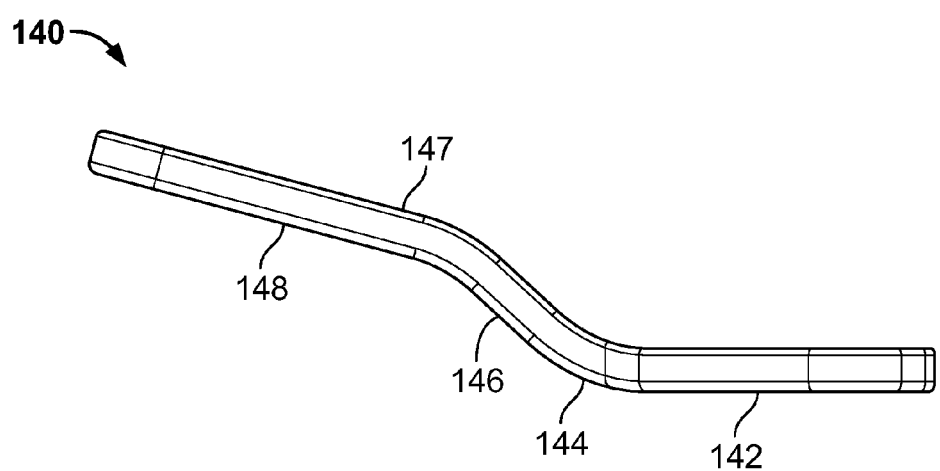
Figure 12:
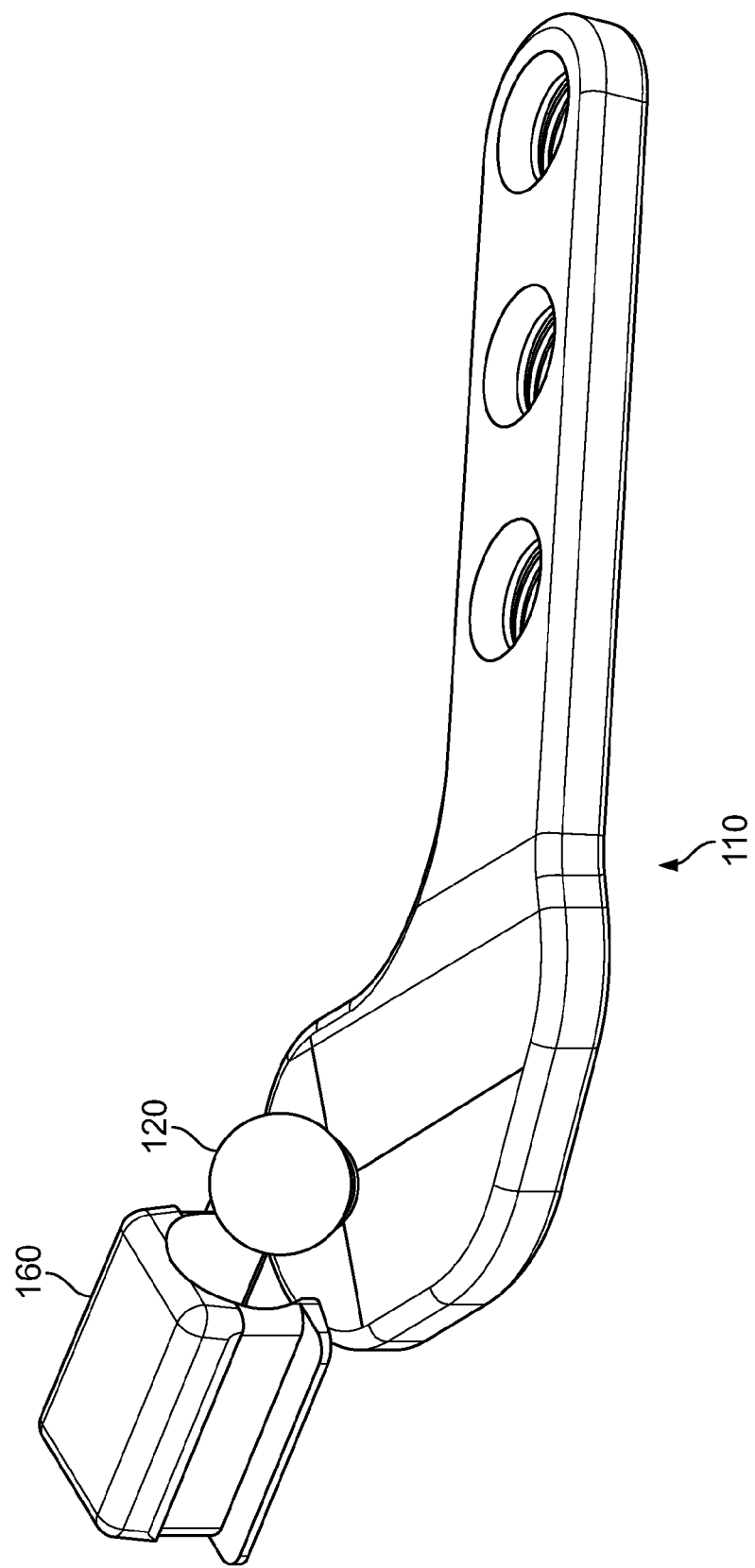
FIG. 12 is a perspective view of the intermediate component positioned to receive the ball attached to the femoral component.
Figure 13:
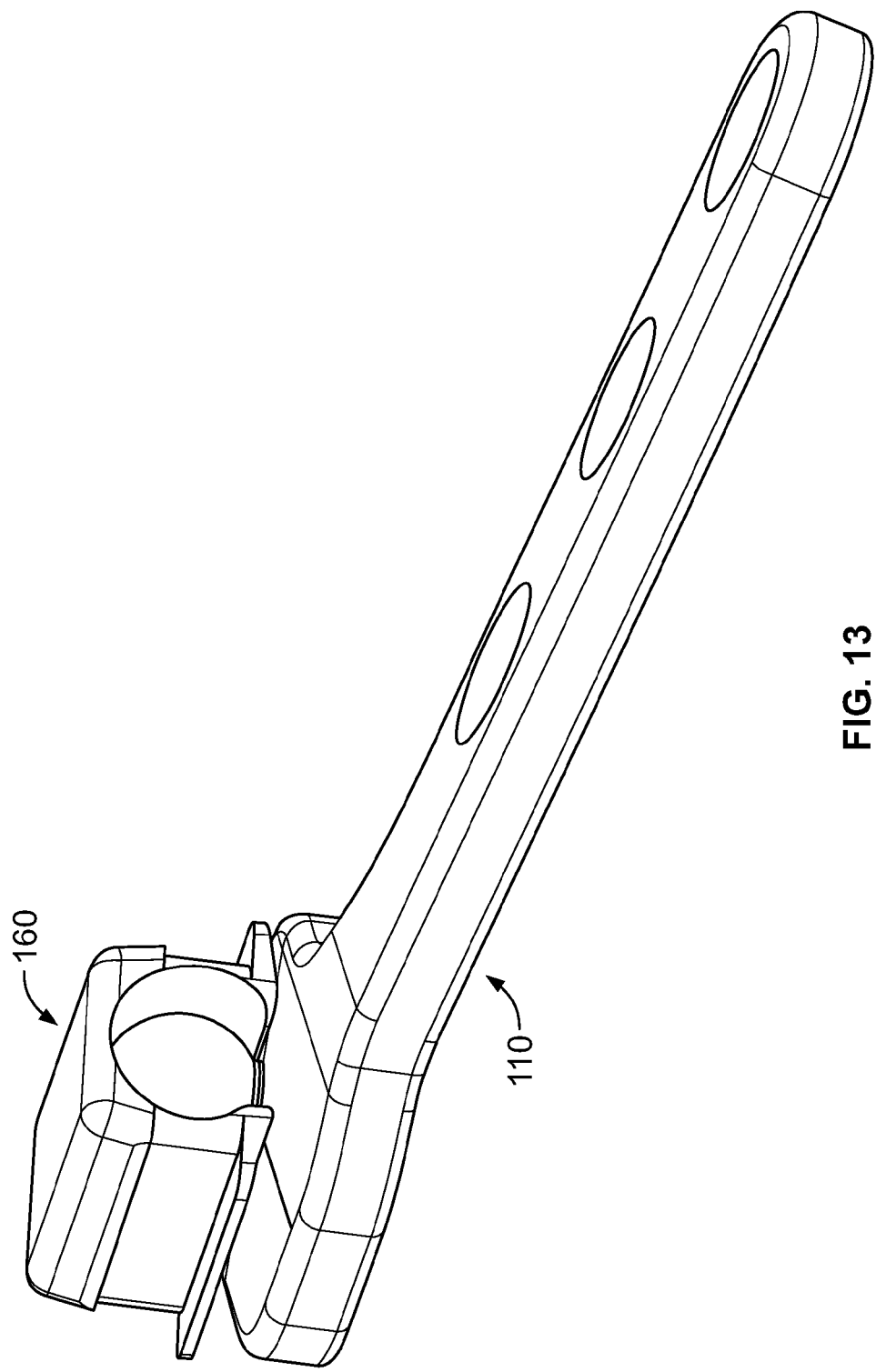
FIG. 13 is a perspective view of the ball positioned in the intermediate component.
Figure 14:
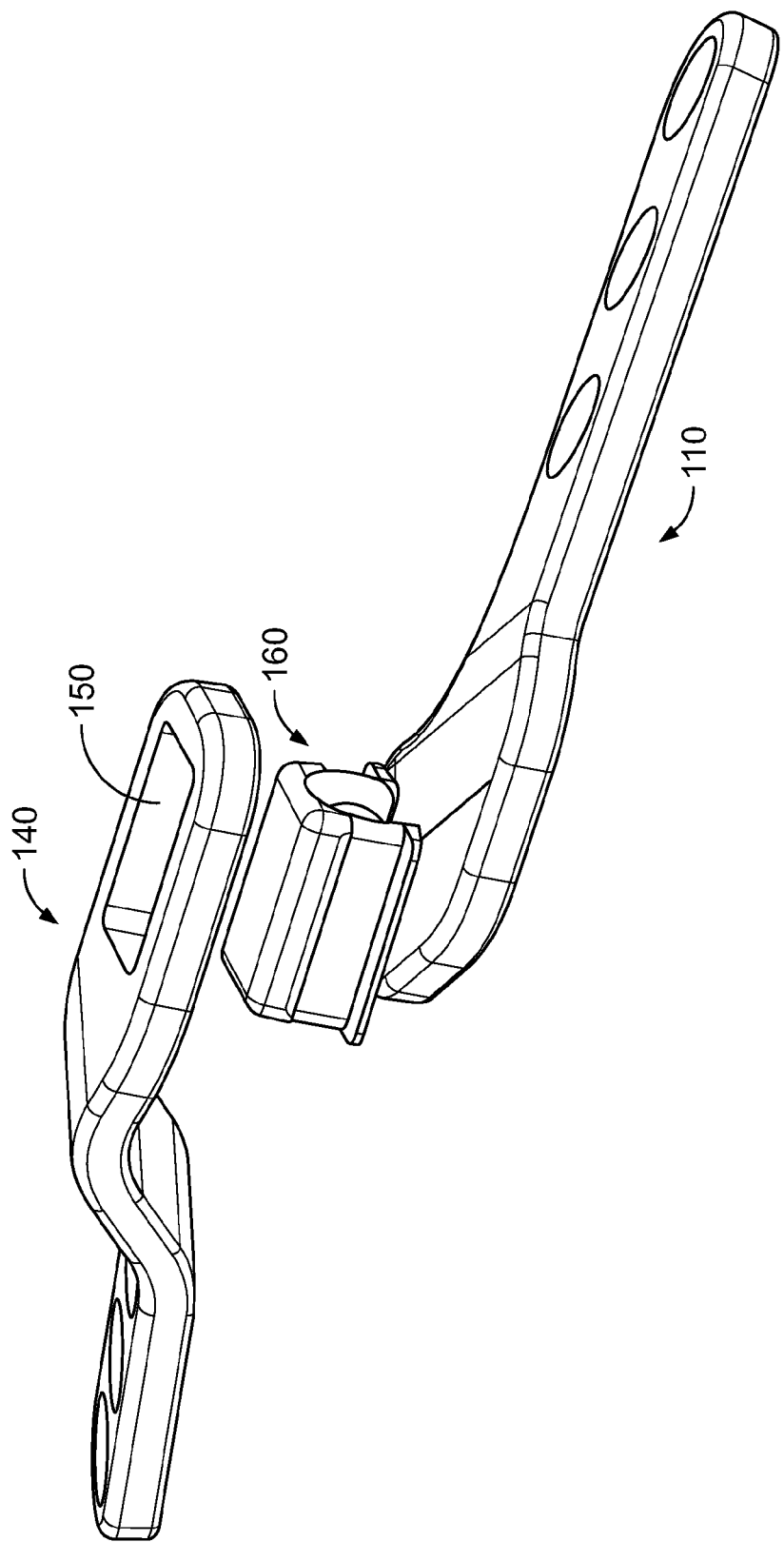
FIG. 14 is a perspective view of the tibial component positioned to receive the intermediate component.
Figure 15:
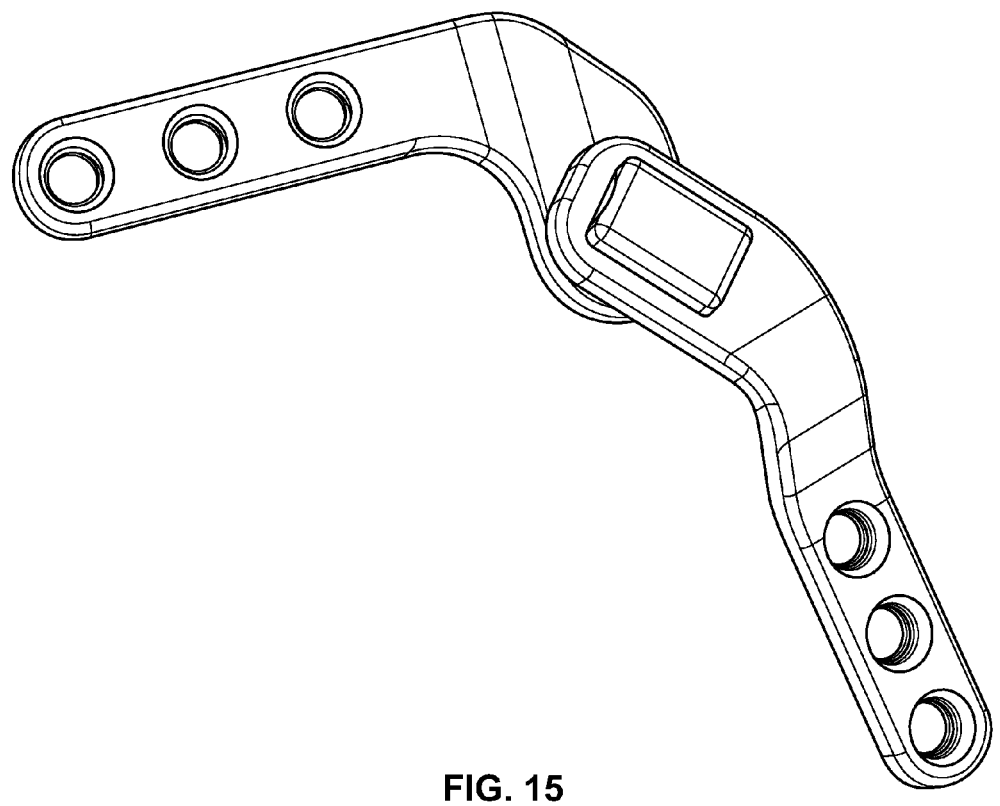
FIG. 15 is another perspective view of a fully assembled apparatus.

FIG. 11A is another perspective view of the tibial component 140. FIG. 11B is a front view of the tibial component 140 showing the slot 150 and apertures 148a, 148b, and 148c. The apertures can be formed in accordance with the apertures described with respect to the femoral component. FIG. 11C is a side view of the tibial component showing a first proximal planar portion 142, a first bend 144, a second central planar potion 146, a second bend 147, and a third distal planar portion 148. FIG. 12 is a perspective view showing the insert component 160 positioned to slide over and engage with ball 120 attached to the femoral component 110. FIG. 13 is a perspective view showing the ball attached to the femoral component engaged within the insert component 160. FIG. 14 is a perspective view of the tibial component 140 positioned to receive the insert component 160 into rectangular slot 150. FIG. 15 is a perspective view showing the fully engaged device.

The components of the apparatus, such as the femoral and tibial components, or plates, can be either machined from a solid piece of material or they can be stamped using a stamping tool and then finished with machining operations, as is known in the art. Similarly, the insert component can be created by molding and/or machining.

While the components of the apparatus could be sold separately and assembled by a user such as a surgeon, the apparatus will generally be sold preassembled as a unit. The preassembled apparatus will be installed in an animal by attaching the femoral plate and tibial plate, respectively, to the femur and tibia of an animal.

A modular device, surgically implanted on a temporary or permanent basis that stabilizes a quadruped stifle joint that is unstable due to cranial cruciate ligament rupture, or avulsion that is either partial or complete.

A modular device, surgically implanted on a temporary or permanent basis that stabilizes a quadruped stifle joint that is unstable due to caudal cruciate ligament rupture, or avulsion that is either partial or complete.

A modular device, surgically implanted on a temporary or permanent basis that stabilizes a quadruped stifle joint that is unstable due to medial collateral ligament rupture, or avulsion that is either partial or complete.

A modular device, surgically implanted on a temporary or permanent basis that stabilizes a quadruped stifle joint that is unstable due to lateral collateral ligament rupture, or avulsion that is either partial or complete.

A modular device surgically implanted on a temporary or permanent basis that stabilizes a quadruped stifle joint that has suffered a traumatic, or congenital medial patellar luxation.

A modular device, surgically implanted on a temporary or permanent basis that stabilizes a quadruped stifle that has suffered a traumatic or congenital lateral patellar luxation.

A modular device, surgically implanted on a temporary basis that stabilizes a quadruped stifle joint that has suffered a traumatic or congenital patellar tendon avulsion, or patellar fracture.

A modular device, surgically implanted on a temporary or permanent basis that stabilizes a quadruped stifle that has suffered a traumatic fracture to either the distal femur, or proximal tibia.

A modular device, surgically implanted on a temporary or permanent basis that stabilizes a quadruped stifle that has suffered any combination, or all of the above conditions.

The invention claimed is:

1. A stifle stabilization system, comprising:
 a femoral component having a leg portion and bottom portion, the bottom portion including an interconnected ball and stem protruding therefrom;
 an articular sliding insert component defining a cylindrical channel corresponding in size and shape to the ball; and
 a tibial component having a first proximal planar portion defining a slot, the slot being of corresponding and complementary shape to sidewalls of the articular sliding insert component to receive the articular sliding insert component therein in a pressure fit engagement,
 wherein, when the channel receives the ball and the articular sliding insert component is received in the slot of the tibial component, the tibial component closes an end of the channel to retain the ball in the channel, and the tibial component is interlocked with the femoral component with translational and rotational movement therebetween.

2. The system of claim 1, wherein the system, when surgically implanted, stabilizes an unstable quadruped stifle joint during all phases of a stride and allows for normal stifle flexion, extension, internal rotation, external rotation, and joint compression.

3. The system of claim 1, wherein the leg portion of the femoral component includes attachment holes for attachment to a femur.

4. The system of claim 1, wherein the femoral component conforms and is permanently attached to a contour of a medial third of a distal femur.

5. The system of claim 1, wherein the femoral component conforms and is temporarily attached to a contour of a medial third of a distal femur.

6. The system of claim 1, wherein the leg portion and bottom portion form an angle with respect to one another.

7. The system of claim 1, wherein the bottom portion of the femoral component includes an aperture, and the stem is retained within the aperture.

8. The system of claim 7, wherein the stem is pressure fit into the aperture.

9. The system of claim 1, wherein the tibial component conforms and is attached to contours of a proximal medial tibia.

10. The system of claim 1, wherein the tibial component has a first proximal planar portion, a second central planar portion, and a third distal planar portion, with a first bend between the first proximal planar portion and second central planar portion, and a second bend between the second central planar portion and third distal planar portion.

11. The system of claim 10, wherein the third distal planar portion of the tibial component contains attachment holes for attachment to a tibia.

12. The system of claim 1, wherein the articular sliding insert component further comprises flange extensions protruding outwardly from a lower portion of sidewalls.

13. The system of claim 1, wherein the ball of the femoral component is slidable along a length of the channel of the articular sliding component when the ball is retained in the channel.

14. A stifle stabilization system, comprising:
a femoral component having one or more attachment holes and an interconnected ball and stem protruding therefrom;
an articular sliding insert component defining a cylindrical channel corresponding in size and shape to the ball; and
a tibial component having one or more attachment holes and defining a slot, the slot being of corresponding and complementary shape to sidewalls of the articular sliding insert component to receive the articular sliding insert component therein in a pressure fit engagement.

15. The system of claim 14, wherein the system, when surgically implanted, stabilizes an unstable quadruped stifle joint during all phases of a stride and allows for normal stifle flexion, extension, internal rotation, external rotation, and joint compression.

16. The system of claim 14, wherein the leg portion of the femoral component includes attachment holes for attachment to a femur.

17. The system of claim 14, wherein the femoral component conforms to contours of a femur.

18. The system of claim 14, wherein the leg portion and bottom portion form an angle with respect to one another.

19. The system of claim 14, wherein the tibial component conforms to contours of a tibia.

20. The system of claim 14, wherein the tibial component has a first proximal planar portion, a second central planar portion, and a third distal planar portion, with a first bend between the first proximal planar portion and second central planar portion, and a second bend between the second central planar portion and third distal planar portion.

21. The system of claim 20, wherein the third distal planar portion of the tibial component contains attachment holes for attachment to a tibia.

22. The system of claim 14, wherein the cylindrical channel of the articular sliding insert component is sized and shaped to receive the ball of the femoral component in slidable engagement along a length of the channel.

* * * * *